(12) United States Patent
Solar et al.

(10) Patent No.: US 7,789,846 B2
(45) Date of Patent: *Sep. 7, 2010

(54) SYSTEM AND METHODS FOR SELECTIVE THERMAL TREATMENT

(75) Inventors: Ronald J. Solar, San Diego, CA (US); Glen Lieber, Poway, CA (US)

(73) Assignee: Thermopeutix, Inc., San Diego, CA (US)

( * ) Notice: Subject to any disclaimer, the term of this patent is extended or adjusted under 35 U.S.C. 154(b) by 69 days.

This patent is subject to a terminal disclaimer.

(21) Appl. No.: 11/041,701

(22) Filed: Jan. 25, 2005

(65) Prior Publication Data

US 2006/0167398 A1    Jul. 27, 2006

(51) Int. Cl.
*A61M 37/00* (2006.01)

(52) U.S. Cl. ............ 604/4.01; 604/6.13; 604/6.16; 604/96.01; 604/113

(58) Field of Classification Search ........... 604/4.01, 604/6.13, 6.16, 7, 8, 27, 96.01, 102.01, 102.03, 604/113, 114

See application file for complete search history.

(56) References Cited

U.S. PATENT DOCUMENTS

| | | | |
|---|---|---|---|
| 380,626 A | 4/1888 | Hamilton |
| 697,181 A | 4/1902 | Smith |
| 2,112,737 A | 3/1938 | Dodge |
| 2,257,369 A | 9/1941 | Davis |
| 3,220,414 A | 11/1965 | Johnston |
| 3,298,371 A | 1/1967 | Lee |
| 3,425,419 A | 2/1969 | Dato |
| 3,504,674 A | 4/1970 | Swenson |
| 3,885,561 A | 5/1975 | Cami |
| 3,888,249 A | 6/1975 | Spencer |
| 3,897,790 A | 8/1975 | Magilton et al. |
| 3,931,822 A | 1/1976 | Marici |
| 3,971,383 A | 7/1976 | van Gerven |
| 4,149,535 A | 4/1979 | Volder |
| 4,224,929 A | 9/1980 | Furihata |
| 4,427,009 A | 1/1984 | Wells et al. |
| 4,445,892 A | 5/1984 | Hussein et al. |

(Continued)

FOREIGN PATENT DOCUMENTS

SU    806 029    2/1981

(Continued)

OTHER PUBLICATIONS

Schwartz et al., Isolated cerebral hypothermia by single carotid artery perfusion of extracorporeally cooled blood in baboons, Neurosurgery: 39(3), 1996.

(Continued)

*Primary Examiner*—Kevin C Sirmons
*Assistant Examiner*—Bhisma Mehta
(74) *Attorney, Agent, or Firm*—Daniel J. Swirsky; AlphaPatent Associates Ltd.

(57) ABSTRACT

Systems and methods for selective cooling of a target site include a catheter having a supply lumen and a delivery lumen, with inlet and exit ports. Blood is withdrawn from the supply lumen and cooled or heated in a control unit. The treated blood is sent to the targeted area via delivery lumen. The supply lumen can act as an insulator for the delivery lumen.

51 Claims, 9 Drawing Sheets

U.S. PATENT DOCUMENTS

| | | | |
|---|---|---|---|
| 4,447,227 A | 5/1984 | Kotsanis | |
| 4,549,879 A | 10/1985 | Groshong et al. | |
| 4,573,966 A | 3/1986 | Weikl et al. | |
| 4,863,441 A | 9/1989 | Lindsay et al. | |
| 4,883,455 A | 11/1989 | Leonard | |
| 4,892,099 A | 1/1990 | Ohkawa et al. | |
| 4,894,164 A | 1/1990 | Polaschegg | |
| 4,904,237 A | 2/1990 | Janese | |
| 4,990,139 A | 2/1991 | Jang | |
| 5,000,734 A | 3/1991 | Boussignac et al. | |
| 5,019,042 A | 5/1991 | Sahota | |
| 5,021,044 A | 6/1991 | Sharkawy | |
| 5,024,668 A | 6/1991 | Peters et al. | |
| 5,106,363 A | 4/1992 | Nobuyoshi | |
| 5,147,332 A | 9/1992 | Moorehead | |
| 5,147,355 A | 9/1992 | Friedman et al. | |
| 5,149,321 A | 9/1992 | Klatz et al. | |
| 5,150,706 A | 9/1992 | Cox et al. | |
| 5,180,364 A | 1/1993 | Ginsburg | |
| 5,188,596 A | 2/1993 | Condon et al. | |
| 5,190,539 A | 3/1993 | Fletcher et al. | |
| 5,207,655 A | 5/1993 | Sheridan | |
| 5,211,631 A | 5/1993 | Sheaff | |
| 5,224,938 A | 7/1993 | Fenton, Jr. | |
| 5,234,405 A | 8/1993 | Klatz et al. | |
| 5,257,977 A | 11/1993 | Eshel | |
| 5,269,749 A | 12/1993 | Koturov | |
| 5,269,758 A | 12/1993 | Taheri | |
| 5,281,215 A | 1/1994 | Milder | |
| 5,334,193 A | 8/1994 | Nardella | |
| 5,364,376 A | 11/1994 | Horzeski et al. | |
| 5,383,854 A | 1/1995 | Safar et al. | |
| 5,395,314 A | 3/1995 | Klatz et al. | |
| 5,403,281 A | 4/1995 | O'Neill et al. | |
| 5,423,807 A | 6/1995 | Milder | |
| 5,462,521 A | 10/1995 | Brucker et al. | |
| 5,486,204 A | 1/1996 | Clifton | |
| 5,486,208 A | 1/1996 | Ginsburg | |
| 5,558,644 A | 9/1996 | Boyd et al. | |
| 5,573,532 A | 11/1996 | Chang et al. | |
| 5,584,804 A | 12/1996 | Klatz et al. | |
| 5,607,444 A * | 3/1997 | Lam | 606/194 |
| 5,624,392 A | 4/1997 | Saab | |
| 5,626,564 A | 5/1997 | Zhan et al. | |
| 5,709,654 A | 1/1998 | Klatz et al. | |
| 5,738,666 A | 4/1998 | Watson et al. | |
| 5,807,391 A | 9/1998 | Wijkamp | |
| 5,820,593 A | 10/1998 | Safar et al. | |
| 5,826,621 A | 10/1998 | Jemmott | |
| 5,827,222 A | 10/1998 | Klatz et al. | |
| 5,868,703 A | 2/1999 | Bertolero et al. | |
| 5,879,316 A | 3/1999 | Safar et al. | |
| 5,879,329 A | 3/1999 | Ginsburg | |
| 5,906,588 A | 5/1999 | Safar et al. | |
| 6,033,383 A | 3/2000 | Ginsburg | |
| 6,042,559 A | 3/2000 | Dobak | |
| 6,056,723 A | 5/2000 | Donlon | |
| 6,090,069 A | 7/2000 | Walker | |
| 6,110,145 A | 8/2000 | Macoviak | |
| 6,126,680 A | 10/2000 | Wass | |
| 6,126,684 A | 10/2000 | Gobin et al. | |
| 6,325,818 B1 | 12/2001 | Werneth | |
| 6,383,172 B1 | 5/2002 | Barbut | |
| 6,435,189 B1 * | 8/2002 | Lewis et al. | 128/898 |
| 6,436,071 B1 | 8/2002 | Schwartz | |
| 6,508,777 B1 * | 1/2003 | Macoviak et al. | 604/4.01 |
| 6,520,988 B1 | 2/2003 | Colombo et al. | |
| 6,605,106 B2 | 8/2003 | Schwartz | |
| 6,743,196 B2 * | 6/2004 | Barbut et al. | 604/101.01 |
| 6,758,832 B2 | 7/2004 | Barbut et al. | |
| 2004/0006299 A1 | 1/2004 | Barbut | |
| 2004/0236350 A1 | 11/2004 | Lewis et al. | |
| 2005/0228359 A1 | 10/2005 | Doyle | |
| 2006/0167399 A1 | 7/2006 | Solar et al. | |

FOREIGN PATENT DOCUMENTS

| | | |
|---|---|---|
| WO | WO 98/26831 | 6/1998 |
| WO | WO 98/31312 | 7/1998 |
| WO | WO 2006/081288 | 8/2006 |

OTHER PUBLICATIONS

Schwartz et al., Selective cerebral hypothermia by means of transfemoral internal carotid artery catheterization, Radiology: 201(2), 1996.

Lownie et al., Extracorporeal femoral to carotid artery perfusion in selective brain cooling for a giant aneurysm, Journal of Neurosurgery: 100, 2004, pp. 343-347.

Schwartz et al, Selective brain cooling decreases cerebral infarct volume, Anesthesiology abstract, Oct. 17, 2000—presented as poster presentation.

In the U.S. Patent and Trademark Office, Notice of Allowance in re: U.S. Appl. No. 11/338,892, dated Jan. 25, 2010, 7 pages.

In the U.S. Patent and Trademark Office, Examiner Interview Summary in re: U.S. Appl. No. 11/338,892, dated Jan. 25, 2010, 2 pages.

In the U.S. Patent and Trademark Office, Office Action in re: U.S. Appl. No. 11/338,892, dated Oct. 9, 2009, 5 pages.

In the U.S. Patent and Trademark Office, Final Office Action in re: U.S. Appl. No. 11/338,892, dated Aug. 28, 2009, 10 pages.

In the U.S. Patent and Trademark Office, Office Action in re: U.S. Appl. No. 11/338,892, dated Jan. 16, 2009, 10 pages.

In the U.S. Patent and Trademark Office, Final Office Action in re: U.S. Appl. No. 11/338,892, dated Jun. 4, 2008, 8 pages.

In the U.S. Patent and Trademark Office, Office Action in re: U.S. Appl. No. 11/338,892, dated Dec. 6, 2007, 10 pages.

In the U.S. Patent and Trademark Office, Restriction Requirement in re: U.S. Appl. No. 11/338,892, dated Aug. 24, 2007, 7 pages.

\* cited by examiner

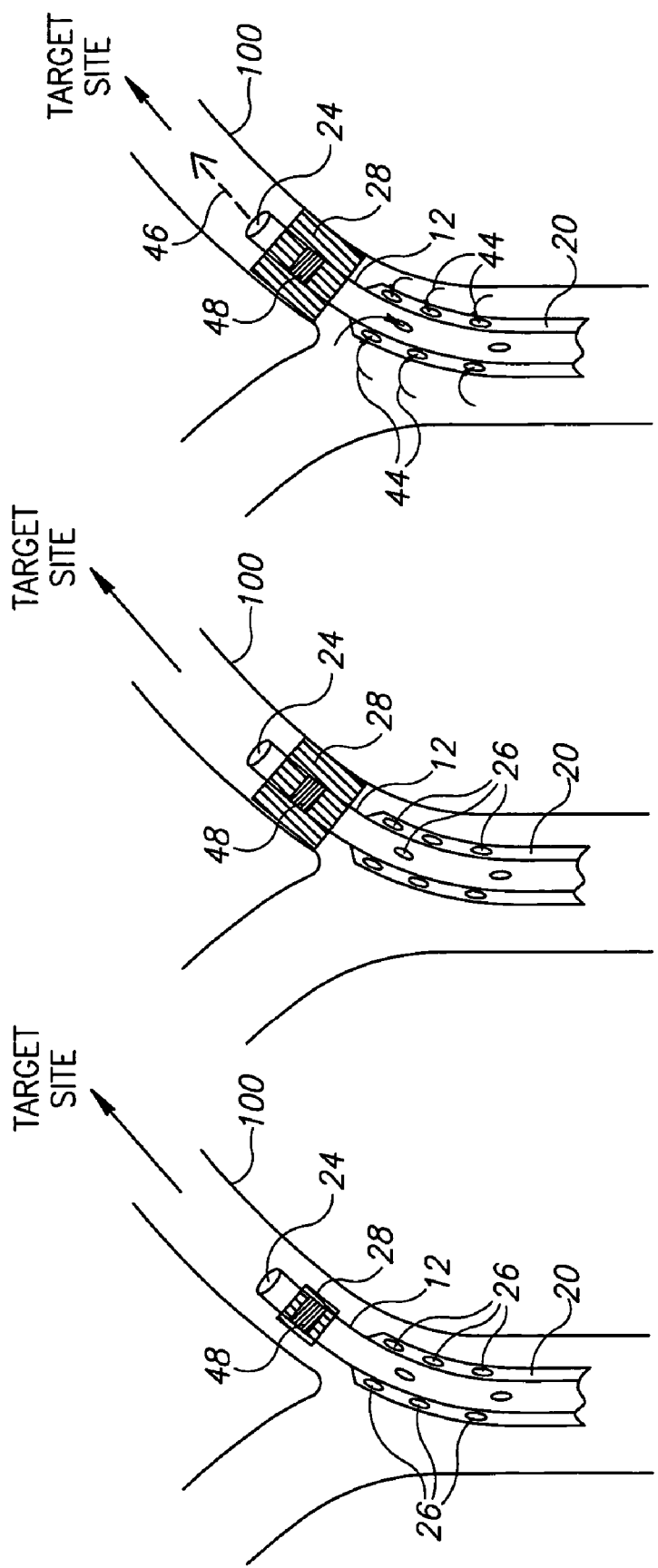

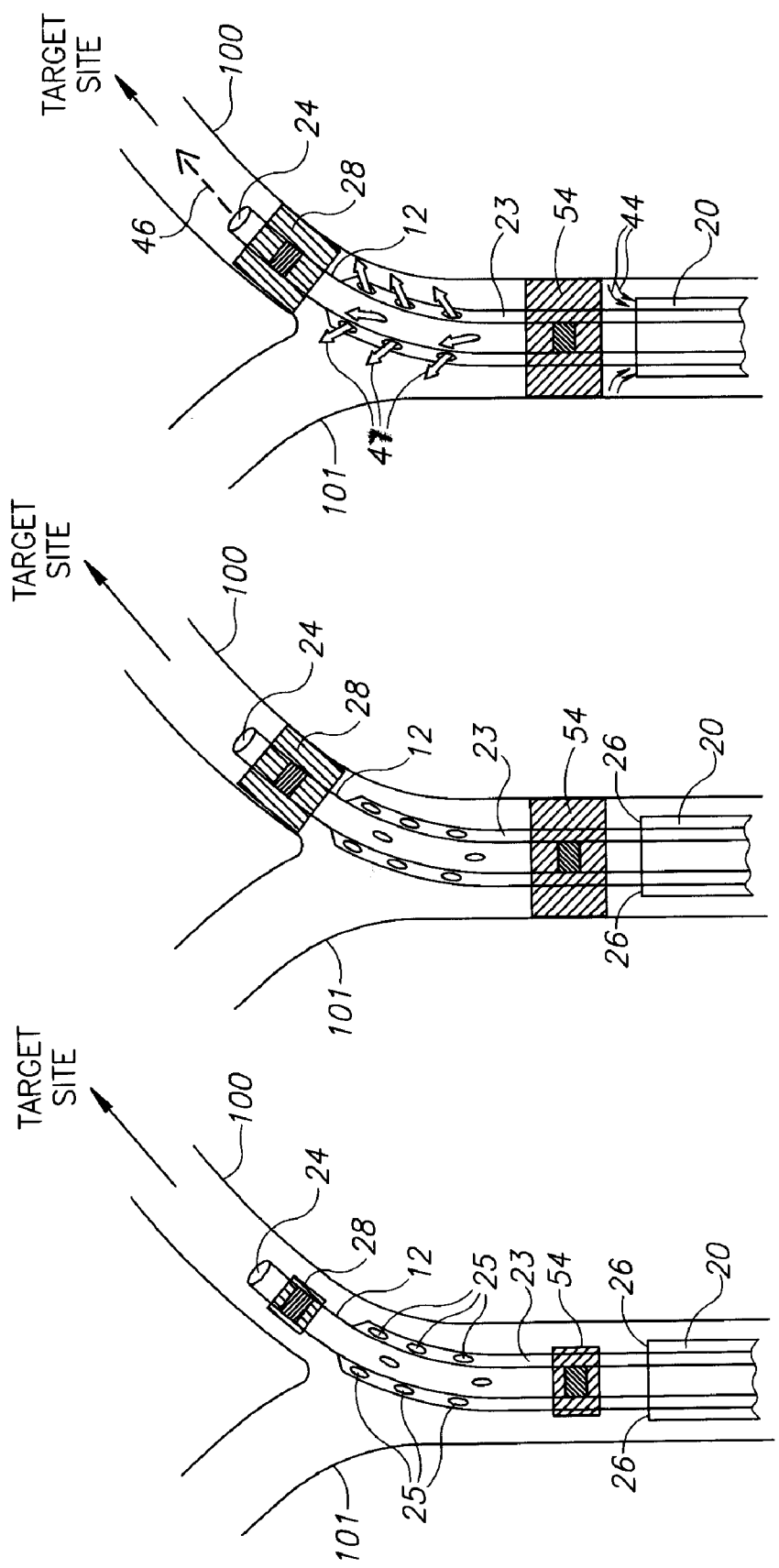

SYSTEM AND METHODS FOR SELECTIVE THERMAL TREATMENT

FIELD AND BACKGROUND OF THE INVENTION

The present invention relates to systems and methods for selectively treating a target site in the body, specifically by changing a temperature thereof, and without significantly affecting other parts of the body.

It is generally known that many disease states and injuries respond favorably to the application of heat and/or cold. For example, hypothermia, i.e. cooling, can reduce blood flow, inflammation and edema, and may alter a variety of effects of ischemia. On the cellular level, hypothermia and hyperthermia (heating) have the ability to effect metabolic and enzymatic activity, reactive oxidant production and gene expression. A number of experimental studies of ischemic stroke have shown that hypothermia reduces the extent of neurologic damage and improves neurologic function.

Prior art methods to effect hypothermia or hyperthermia have a number of disadvantages. Most of these methods primarily involve the entire body by employing surface techniques or systemic intravascular perfusion. U.S. Pat. No. 5,624,392 to Saab and U.S. Pat. No. 6,033,383 to Ginsburg teach the use of heat transfer catheters that are placed into the venous side of the vascular system. These devices cool or heat venous blood passing over them, and the heated or cooled blood is distributed throughout the entire body. Such methods have serious limitations. For example, systemic hypothermia causes shivering, which increases the metabolic rate and may cause serious disturbances of the cardiovascular system. Surface techniques are slow, have limited heating/cooling capability, and require apparatus that can interfere with the ability to perform a medical procedure. In addition, none of these prior art techniques have the ability to control changes in blood flow and pressure that can result from the application of hypothermia or hyperthermia, nor do they have means to administer pharmacologic agents selectively to the target area.

Other prior art methods designed to selectively treat an area without adversely affecting the rest of the body have been disclosed. For example, U.S. Pat. Nos. 6,436,071 and 6,605,106 to Schwartz, teach a catheter for intravascular corporeal cooling, designed to eliminate problems that develop due to complications from high pressure within a delivery catheter. This disclosure teaches the use of a pressure relief valve, which has the disadvantage of a likelihood of total body cooling upon activation of the valve. Additionally, long-term effects of the disclosed system can include potential local vascular damage, and additional total body cooling, since arterial blood passing over the cooling catheter would itself be cooled. U.S. Pat. No. 6,042,559 to Dobak teaches a method and apparatus for performing hypothermia without significant effect on surrounding organs or other tissues. The disclosed apparatus includes a flexible supply catheter, and a separate flexible delivery catheter—one used for removing the blood and one used for delivering cooled blood into an artery feeding the selected organ. The delivery catheter has a layer of insulation. However, the use of two catheters increases the risk of vascular complications, the complexity of the procedure, and the time to effect cooling of the target organ.

There is thus a widely recognized need for, and it would be highly advantageous to have, a method and system for selective thermal treatment which is devoid of the above limitations.

SUMMARY OF THE INVENTION

According to one aspect of the present invention, there is provided a system for providing selective thermal therapy. The system includes a first lumen having a distal end and a proximal end, an exit port located on the first lumen, an occlusion element positioned on the first lumen, proximal to the exit port, a second lumen coaxial to the first lumen, the second lumen having a proximal end and a distal end, a second port positioned on the second lumen, the second port proximal to the occlusion element, and a control unit in fluid communication with the proximal ends of the first lumen and the second lumen.

According to another aspect of the present invention, there is provided a device for providing selective thermal therapy. The device includes a supply lumen for delivering normothermal blood to a location outside of the body, a delivery lumen for supplying thermally treated blood to a target site in the body, wherein the supply lumen is positioned around a portion of the delivery lumen and wherein the thermally treated blood is the normothermal blood after a thermal adjustment, and an occlusion element positioned on the delivery lumen in a location which is proximal to a distal end of the delivery lumen and distal to a distal end of the supply lumen.

According to another aspect of the present invention, there is provided a device for providing selective thermal therapy. The device includes a first lumen having a distal end and a proximal end, an exit port located on the first lumen, a first occlusion element positioned on the first lumen, distal to the exit port, a second lumen coaxial to the first lumen, the second lumen having a proximal end and a distal end, a second occlusion element positioned on the second lumen, and a second port positioned on the second lumen, the second port proximal to the second occlusion element.

According to another aspect of the present invention, there is provided a method for selectively cooling or heating a part of a body. The method includes providing a device for insertion into a vessel, the device having a first lumen having an exit port, a second lumen having a second port, the second lumen positioned coaxial to the first lumen, and an occlusion element positioned between the exit port and the second port, inserting the device into a vessel, expanding the occlusion element so as to separate between a first area in fluid communication with the exit port and a second area in fluid communication with the second port, withdrawing normothermic blood from the second area via the second port and through the second lumen, delivering the normothermic blood to a control unit, thermally treating the normothermic blood in the control unit to obtain thermally treated blood, and delivering the thermally treated blood to the first area via the first lumen and the exit port.

According to another aspect of the present invention, there is provided a method for providing insulated thermally treated blood to a location in the body, the method including providing a delivery catheter and providing an insulating layer around the delivery catheter, the insulating layer being a conduit for insulating blood, the insulating blood being of a different temperature than the thermally treated blood.

According to further features in preferred embodiments of the invention described below, the first lumen is a delivery lumen for delivering thermally treated blood to a target site in the body. In one embodiment, the exit port is located at the distal end of the first lumen. In another embodiment, the exit port is located proximal to the distal end of the first lumen.

According to further features in preferred embodiments of the invention, the occlusion element has an atraumatic surface, and may include a hydrophilic coating, a drug coating, or both. The occlusion element may be a balloon, or alternatively, the occlusion element is a mechanically expandable device, such as a spring loaded device, or includes a shape memory alloy.

According to further features in preferred embodiments of the invention, the second lumen is a supply lumen for providing normothermal blood to the control unit and the second port is an inlet port, or several inlet ports. In one embodiment, the system and devices further comprise an auxiliary delivery lumen between the first and second lumens and coaxially arranged with respect to the first lumen, the auxiliary delivery lumen having one or several secondary exit port positioned between the exit port and the inlet port. The system may further include a second occlusion element positioned between the secondary exit port and the inlet port.

According to further features in alternative embodiments of the invention, the second lumen is an auxiliary delivery lumen, the second port is one or more secondary exit ports, and the system further includes a supply lumen positioned coaxially with respect to the auxiliary delivery lumen, the supply lumen having one or more inlet ports. In one embodiment, a second occlusion element is positioned between the secondary exit port and the inlet port. In another embodiment, the system further includes an anchoring element at the distal end of the first lumen. The anchoring element can be, for example, a balloon or a bent distal end.

According to further features in preferred embodiments of the invention, the control unit includes a thermal adjustor, and may include a pumping mechanism. The system may further include a physiological sensor positioned at the exit port. The system may also include a pressure lumen and a physiological sensor at a proximal end of the pressure lumen. The physiological sensor is in communication with the control unit, which may be configured to calculate an output based on data received from the physiological sensor. The output may be presented as a display to a user. Furthermore, the output may be used to automatically change a parameter provided by the control unit.

According to further features in preferred embodiments of the invention, the delivering of the thermally treated blood includes pumping. The method can further include delivering a second thermally treated blood to a location in the body, the second thermally treated blood having a different temperature than the thermally treated blood. The method can further include monitoring a physiological parameter and adjusting the thermally treating based on the monitored parameter.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 8A-8C are illustrations of the steps of a method for treating a specific target site in accordance with a preferred embodiment of the present invention;

FIGS. 9A-9C are illustrations of a method for treating a specific target site in accordance with another embodiment of the present invention.

DESCRIPTION OF THE PREFERRED EMBODIMENTS

Figure 1:
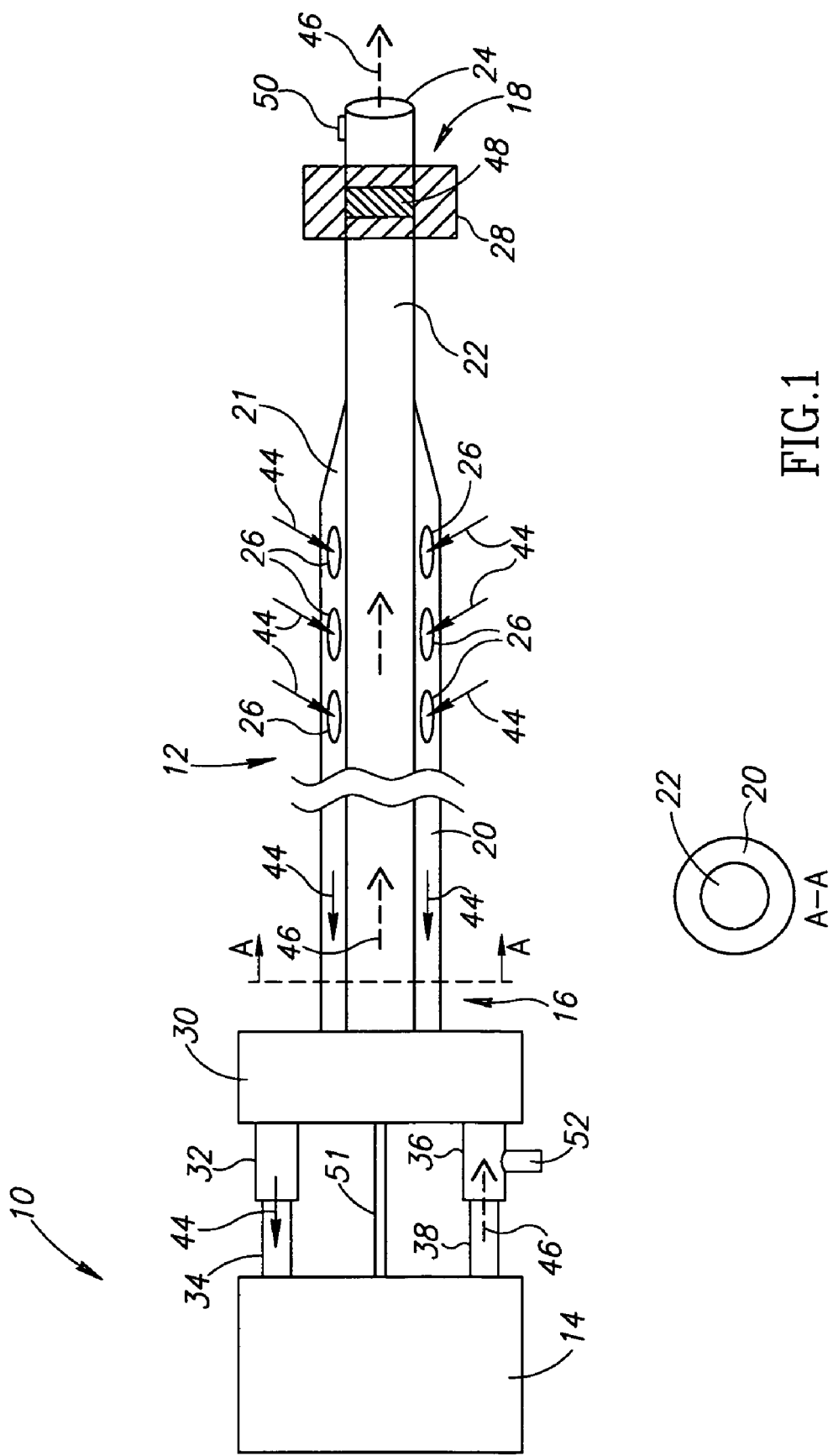
FIG. 1 is an illustration of a system including a catheter and a control unit, in accordance with a preferred embodiment of the present invention.

The present invention is of systems and methods which can be used for selective thermal therapy. Specifically, the present invention can be used to selectively cool or heat a specific organ in the body, using a single catheter for collection and delivery of normothermic and thermally altered blood.

The principles and operation of systems and methods according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates a system 10 for selective cooling or heating of an organ, in accordance with a preferred embodiment of the present invention. System 10 includes a catheter 12 and a control unit 14. Catheter 12 has a proximal end 16 and a distal end 18, and includes a supply lumen 20 and a delivery lumen 22. Delivery lumen 22 extends through an entire length of catheter 12, from proximal end 16 to distal end 18, and has an exit port 24 at or near distal end 18 for delivery of blood to a target site. Delivery lumen 22 may have a first wall defining a first lumen. Supply lumen 20 is positioned coaxially with respect to delivery lumen 22, as shown in cross-section A-A, and extends from proximal end 16 of catheter 12 to an area proximal to distal end 18. Supply lumen 20 may have a second wall where a second or supply lumen is defined as a space between the first wall and the second wall. A distal end 21 of supply lumen 20 is in a vicinity of distal end 18 of delivery lumen 22, as shown in FIG. 1. This configuration provides an insulating layer to delivery lumen 22 along a majority of a length of delivery lumen 22. In an alternative embodiment, supply lumen 20 runs alongside delivery lumen 22. Supply lumen 20 has inlet ports 26 at one or more locations along its length, for receiving normothermic blood from the blood vessel. At least one occlusion element 28 is positioned at or near distal end 18 of catheter 12, proximal to exit port 24 and distal to a distal end 21 of supply lumen 20. The distal end 21 of the supply lumen 20 is positioned relative to the distal end 18 of the delivery lumen 22 such that the distal end 21 of the supply lumen 20 is in proximity to the distal end 18 of the delivery lumen 22 so that the supply lumen 20 acts as the insulating layer along a majority of the length of the delivery lumen 22 when receiving blood from the body. The delivery lumen 22 is insertable into an artery of the body at a peripheral location of the body and adapted to extend to a remote location of the body. A hub 30 for connecting supply lumen 20 and delivery lumen 22 to control unit 14 is located at proximal end 16 of catheter 12. Hub 30 includes an inlet connector 32 for providing supply blood to a supply blood inlet 34 in control unit 14, and an outlet connector 36 for receiving delivery blood from a delivery blood outlet 38 in control unit 14. Control unit 14 thermally alters (i.e. heats or cools) normothermic blood received from supply blood inlet 34, and sends the thermally altered blood out through delivery blood outlet 38. Thus, supply lumen 20, delivery lumen 22 and control unit 14 form a closed loop system for delivering and supplying blood. Catheter 12 can be introduced over a guidewire, either as an over-the-wire system or as a rapid exchange system, or may include a fixed wire at its distal tip. In a preferred embodiment, delivery lumen 22 acts as a guidewire lumen as well. In alternative embodiments, a separate guidewire lumen is positioned alongside or coaxial with delivery lumen 22. In the fixed-wire configuration, catheter 12 could further include a torqueable catheter shaft.

The general cycle of blood flow is as follows. Normothermic blood, depicted by unbroken arrows 44, flows from a blood vessel, through inlet ports 26, and into supply lumen 20. Supply lumen 20 delivers the normothermic blood to control unit 14 via inlet connector 32. Blood is then thermally altered in control unit 14. Delivery lumen 22 receives thermally altered blood, depicted by broken arrows 46, from delivery blood outlet 38 in control unit 14 via outlet connector 36, and delivers the thermally altered blood to the target site in the body. In order to ensure that heating or cooling of the target site is accomplished without causing heating or cooling of other parts of the body, it is necessary to physically separate the collection of normothermic blood from the delivery of thermally altered blood. In order to accomplish this separation using a single device, catheter 12 is designed with both a delivery lumen and a supply lumen which are physically separated from one another by an occlusion element 28. By placing occlusion element 28 between distal end 21 of supply lumen 20 and exit port 24, only the blood proximal to occlusion element 28 enters supply lumen 20, and the thermally altered blood only reaches that part of the cardiovascular system which is distal to occlusion element 28.

Figure 2:
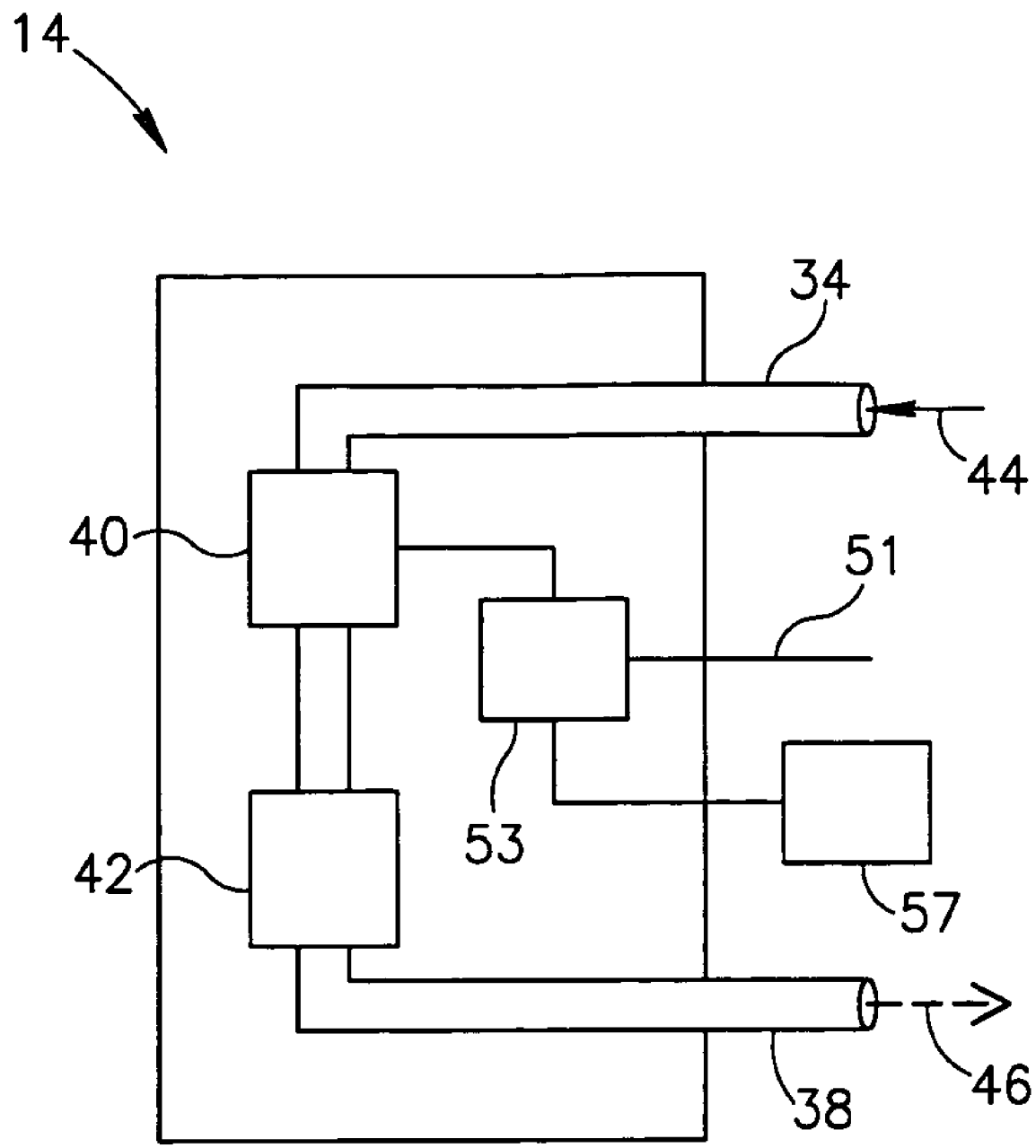
FIG. 2 is a schematic illustration of the control unit of the system of FIG. 1.

Reference is now made to FIG. 2, which is a schematic illustration of control unit 14 in greater detail. Control unit 14 includes supply blood inlet 34 for receiving normothermic blood, depicted by unbroken arrow 44, and delivery blood outlet 38 for delivering thermally altered blood, depicted by broken arrow 46. Control unit 14 further includes a thermal adjustor 40 for changing a temperature of normothermic blood received from supply blood inlet 34, thus producing thermally altered blood. Thermal adjustor 40 can be a heating mechanism, a cooling mechanism, or a combination heating/cooling mechanism which is controllable by a user. In a preferred embodiment, thermal adjustor 40 is a cooling mechanism such as, for example, Medtronic, Inc.'s Bio-Cal® Blood Temperature Control Module or the MYOthermXP® Cardioplegia System. Alternatively, thermal adjustor 40 comprises a coiled tubing in an ice bath. In a preferred embodiment, control unit 14 further includes a pumping mechanism 42 to facilitate delivery of thermally altered blood through delivery blood outlet 38. Pumping mechanism 42 can be, for example, a centrifugal blood pump (Bio-Pump®, Medtronic, Inc.; Sarns™ Centrifugal System, Terumo Cardiovascular Systems) or an electromagnetic pump (Levitronix® CentriMag® Blood Pumping System, Levitronix GmbH). In one embodiment, control unit 14 further comprises a vacuum to assist in withdrawal of the normothermic blood.

In order to more closely monitor physiological parameters during a procedure, sensors 50 may be placed at or near exit port 24, shown schematically in FIG. 1. Sensors 50 can include one or several sensors, capable of measuring pressure, temperature, flow, or a combination thereof. In an alternative embodiment, pressure is measured by providing an additional lumen referred to as a pressure lumen. The pressure lumen has a proximal pressure transducer attached thereto which is capable of measuring the pressure of a column of fluid located within the pressure lumen. Sensors 50 are in communication with control unit 14 via conventional wires 51 or via wireless communication. As shown in FIG. 2, control unit 14 can further include a processor 53 for receiving and processing signals from sensors 50 and providing an output based on the processed signals. Output can be sent to a display 57, which provides output information to a user. The user can make a decision based on this output information regarding further adjustments of the temperature, flow and pressure. Display 57 can be, for example, a visual, audio, numeric or any other suitable display. When a user sees the display, he/she can manually adjust thermal adjustor 40. The user can also decide to immediately stop the procedure if necessary. Alternatively, processor 53 sends output directly to thermal adjustor 40, which then automatically changes cooling or heating parameters based on the output.

In one embodiment, hub 30 further includes an infusion port 52. Infusion port 52 can be used, for example, to introduce contrast media to the site. Alternatively, infusion port 52 can be used to introduce drugs. For example, lytic agents which are typically used to dissolve clots can be introduced via infusion port 52 into an artery, rather than the common practice of intravenous delivery of these agents. Alternatively, in some circumstances it may be desirable to introduce clotting agents, which can be done via infusion port 52. It should be readily apparent that any suitable agent, compound, drug, or substance can be introduced via infusion port 52, and all of these possibilities are included within the scope of the present invention.

Occlusion element 28 is comprised of an atraumatic surface so as not to damage the inner walls of a blood vessel. In a preferred embodiment, occlusion element 28 is comprised of a hydrophilic surface, which by attracting water forms a natural atraumatic layer. Furthermore, a hydrophilic surface can provide means for expanding a folded balloon which is configured to open when in contact with water components from the blood. Occlusion element 28 may further include a coating for providing long-term (measured in hours, days or even months) implantation of catheter 12 in the body. Alternatively or in addition, occlusion element 28 may further include a drug coating. In one embodiment, occlusion element 28 is a balloon, such as is commonly used with catheter systems, and is expandable by introduction of a fluid therein, wherein the fluid can be a liquid or a gas. In this embodiment, a separate inflation lumen is included within catheter 12, either alongside or coaxial with delivery lumen 22, and is in fluid communication with occlusion element 28. Fluid is introduced via an inflation port (not shown) positioned at hub 30. These types of balloons and inflation lumens are commonly known in the art. The balloon may be elastomeric, compliant, semi-compliant or non-compliant, as long as it serves to occlude the vessel without causing damage to the internal walls. In another embodiment, occlusion element 28 is a self-expanding element confined within a retractable sheath, such that upon retraction of the sheath, the self expanding element expands to a diameter sufficient to occlude the vessel. In this embodiment, the sheath is connected to a retractor positioned at proximal end 16 of catheter 12. The self-expanding element may be comprised of an elastic or spring-like material, or a shape-memory alloy. Such materials are known in the art. In another embodiment, occlusion element 28 is a mechanically actuated mechanism, whereby it is expanded by mechanical means. In yet another embodiment, occlusion element 28 is comprised of a temperature sensitive material which can be expanded or retracted by exposure to specific temperatures. Specifically, perfusion of cooled or heated blood through delivery lumen 22 would cause expansion of occlusion element 28, and perfusion of normothermic blood through delivery lumen 22 (such as, for example, during renormalization of temperature) would cause retraction of occlusion element 28. This may be accomplished, for example, by using a shape-memory material, either as occlusion element 28 itself, or as an actuator positioned alongside occlusion element 28. Similarly, this could be accomplished by using a bi-metallic strip.

Occlusion element 28 further includes a radiopaque marker 48 for viewing of a location of catheter 12 generally and occlusion element 28 specifically within the vessel. In one embodiment, occlusion element 28 is itself comprised of radiopaque material. In alternative embodiments, one or more radiopaque markers 48 are positioned on occlusion element 28. Additional radiopaque markers 48 may also be positioned in other places along catheter 12 such as, for example, at distal end 18, or at inlet ports 26.

Figure 3:
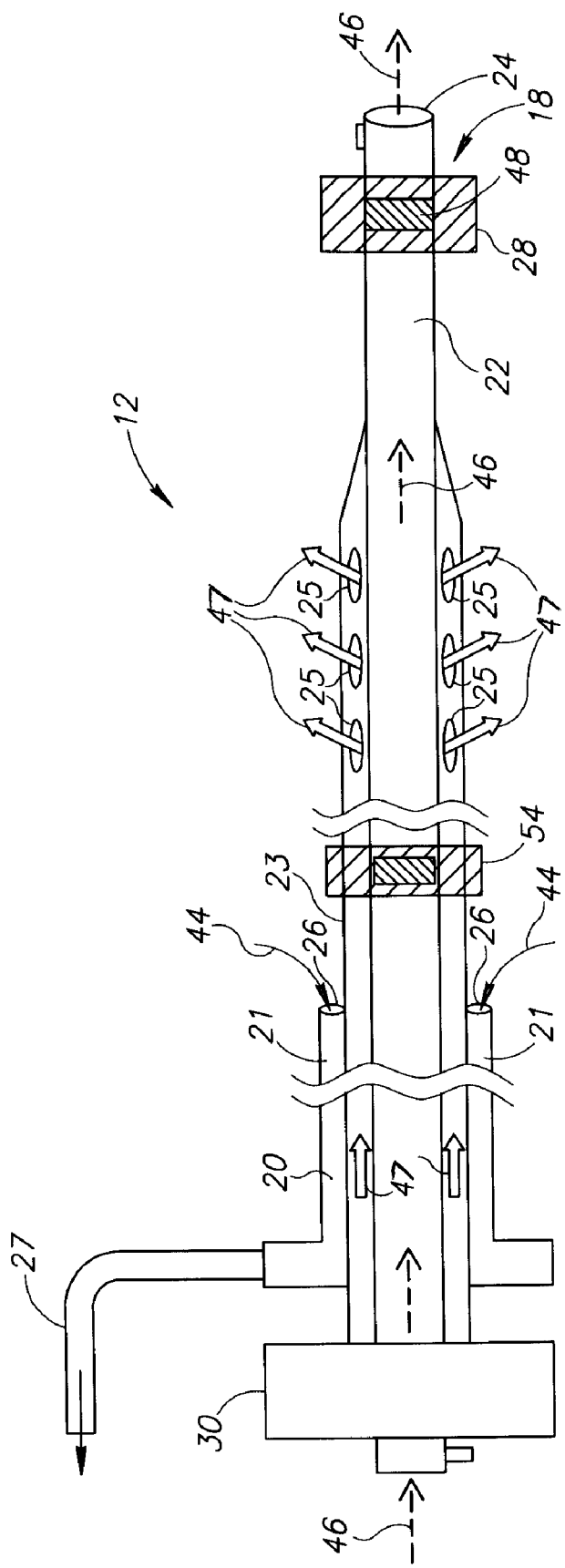
FIG. 3 is an illustration of a catheter in accordance with another embodiment of the present invention.

Reference is now made to FIG. 3, which is an illustration of a catheter 12 in accordance with another embodiment of the present invention. Catheter 12 is similar in construction to catheter 12 shown in FIG. 1, with an additional feature of an auxiliary delivery lumen 23, preferably situated between supply lumen 20 and delivery lumen 22. Auxiliary delivery lumen 23 is configured to receive a supplemental blood flow from control unit 14 and to deliver the supplemental blood (depicted by wide arrows 47) to a vessel. In one embodiment, the supplemental blood is taken from the control unit 14 and introduced into auxiliary delivery lumen 23 at an initial thermally altered temperature. Supplemental blood as depicted by wide arrows 47 undergoes a temperature change during its flow from the proximal end to the distal end of auxiliary delivery lumen due to conduction from the normothermic blood in the blood vessel which is in close proximity thereto. In this embodiment, the temperature of supplemental blood that exits ports 25 of auxiliary delivery lumen 23 is of a different temperature $T_2$ than the temperature $T_1$ of the thermally altered blood depicted by broken arrows 46, which is delivered to the target site. The presence of an additional layer of blood flow in a lumen surrounding delivery lumen 22 provides increased insulation for the thermally altered blood being delivered to the target site. Furthermore, blood from auxiliary delivery lumen 23 can be used for simultaneous treatment of different parts of the body. Thus, for example, if it were desired to treat the target site with one temperature and an additional site with another temperature, auxiliary delivery lumen 23 could be used for treatment of the additional site. The amount of temperature change that occurs within auxiliary delivery lumen 23 depends on the flow rate and the initial temperature difference between the thermally altered blood entering auxiliary delivery lumen 23 and the normothermic blood surrounding auxiliary delivery lumen 23.

In a preferred embodiment, auxiliary delivery lumen 23 is coaxially arranged with respect to delivery lumen 22, and includes secondary exit ports 25, preferably in a distal portion thereof. The distal portion of auxiliary delivery lumen 23 is proximal to exit port 24. Supply lumen 20 is positioned coaxially with respect to auxiliary delivery lumen 23, and distal end 21 of supply lumen 20 is proximal to secondary exit ports 25. In one embodiment, supply lumen 20 is a standard vascular sheath and may have a side arm 27 from which normothermic blood is sent to control unit 14.

A second occlusion element 54 may be positioned proximal to secondary exit ports 25 and distal to inlet ports 26 of supply lumen 20. In this way, a first target site is supplied by thermally altered blood exiting delivery lumen 22 and having a temperature $T_1$, and a second target site is separately supplied by supplemental blood exiting auxiliary delivery lumen 23 and having a temperature $T_2$.

Figure 4A:
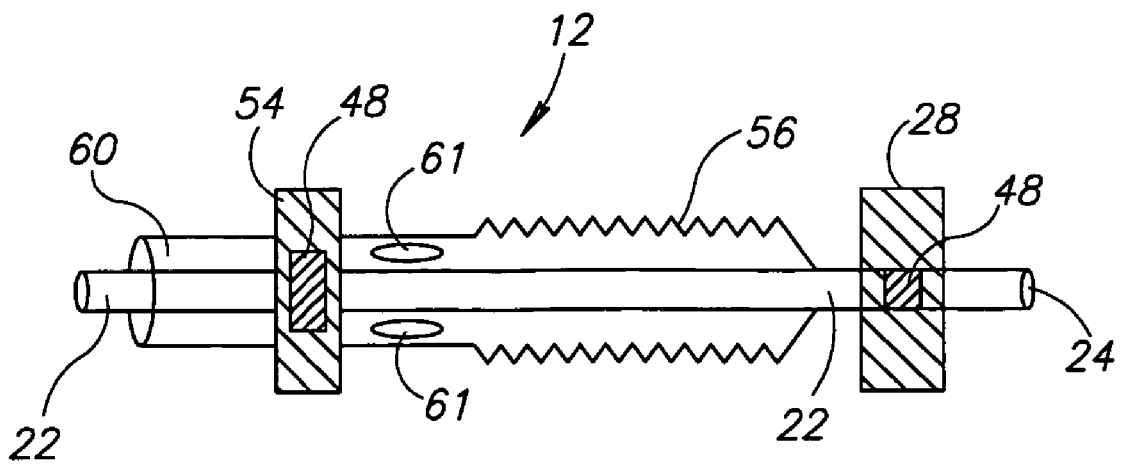
FIGS. 4A and 4B are illustrations of a distal portion of the catheters of FIGS. 1 and 3, having distal ends which are variably positionable.
Figure 4B:
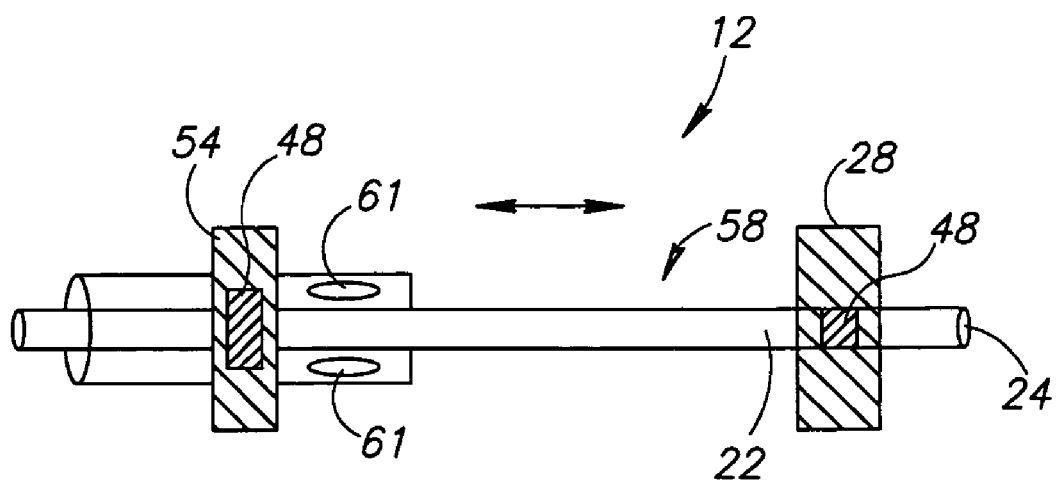

Reference is now made to FIGS. 4A and 4B, which are illustrations of a distal portion of catheter 12, in accordance with another embodiment of the present invention, wherein exit port 24 is positionable at varying distances from ports 61. Ports 61 are inlet or outlet ports of a coaxial lumen 60, which can be any lumen coaxial to delivery lumen 22. In one embodiment, coaxial lumen 60 is supply lumen 20 and ports 61 are inlet ports 26. In another embodiment, coaxial lumen 60 is auxiliary delivery lumen 23, and ports 61 are secondary exit ports 25. Delivery lumen 22 is movable within coaxial lumen 60. Movement can be a twisting motion, for example, wherein delivery lumen 22 and coaxial lumen 60 are attached with a bellows 56, as shown in FIG. 4A. Alternatively, movement can be a sliding motion, wherein delivery lumen 22 and coaxial lumen 60 are attached via telescoping means 58, as shown in FIG. 4B. Any other means for changing a distance between exit port 24 and ports 61 is included within the scope of the invention.

Figure 5C:
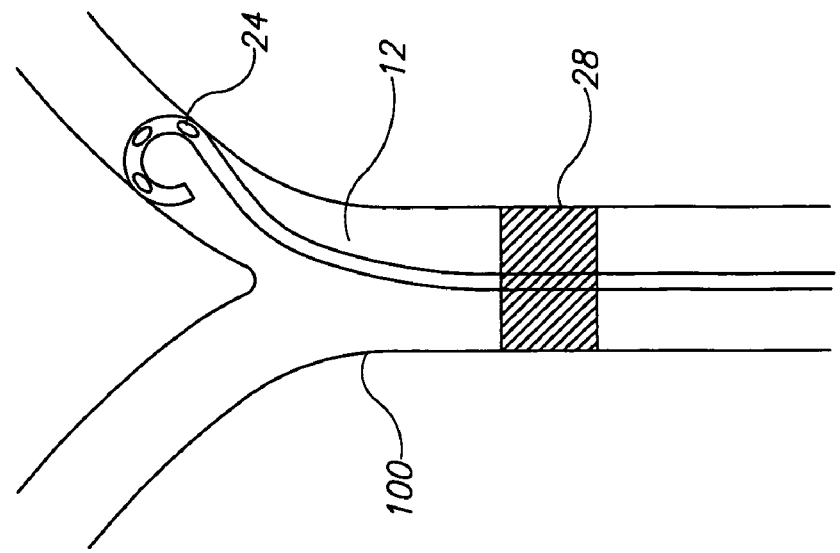
FIGS. 5A-5C are illustrations of a catheter having a bendable distal end, in accordance with one embodiment of the present invention.
Figure 5A:
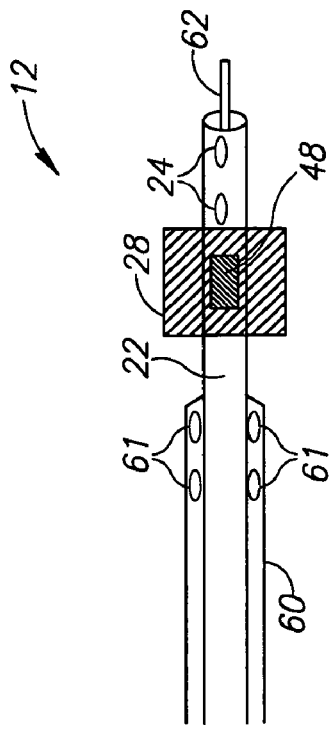
Figure 5B:
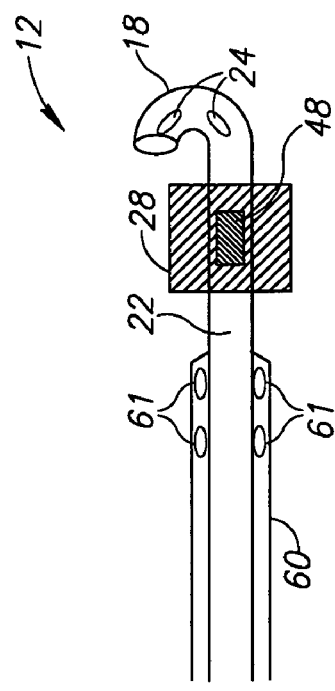

In some instances, it may be desirable to anchor catheter 12 into a vessel, providing greater control and easier accessibility to the target site. Reference is now made to FIGS. 5A-5C, which are illustrations of a catheter having a bendable distal end 18 for anchoring. As shown in FIG. 5A, catheter 12 includes delivery lumen 22 and occlusion element 28. At least one exit port 24 is located distal to occlusion element 28. In one embodiment, exit port 24 is at distal end 18 of catheter 12. In another embodiment, exit port 24 is located anywhere between occlusion element 28 and distal end 18. In one embodiment, distal end 18 is initially in a straightened positioned as it is advanced over a guidewire 62. Guidewire 62 is insertable through delivery lumen 22. Alternatively, guidewire 62 may be insertable through a separate guidewire lumen (not shown), which is either coaxial with or adjacent to delivery lumen 22. Catheter 12 is advanced over guidewire 62 until a desired location is reached. Guidewire 62 is then removed, allowing catheter 12 to assume a bent configuration, as depicted in FIG. 5B. The bent configuration is suitable for anchoring in a vessel, as shown schematically in FIG. 5C. In an alternative embodiment, catheter 12 has a fixed wire at its distal end, and distal end 18 is initially straightened by inserting a removable stylet. Once the desired location is reached, the stylet is removed, causing distal end 18 to assume its bent configuration. In one embodiment, distal end 18 is comprised of a shape memory alloy.

Alternatively, it may be desirable to anchor catheter 12 in a vessel other than the one leading to the target site. For example, if catheter 12 is anchored in a branch vessel, thermally altered blood can be diverted into the main vessel by strategically placing exit port 24 at a specific location or locations.

Figure 6:
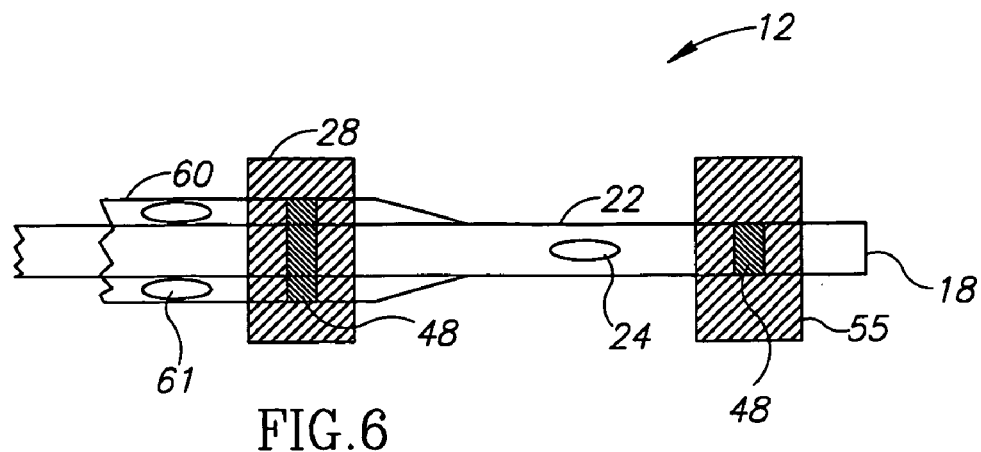
FIG. 6 is an illustration of a catheter which is suitable for anchoring in a separate vessel in accordance with one embodiment of the present invention.

Reference is now made to FIG. 6, which is an illustration of catheter 12 suitable for anchoring in a separate vessel, in accordance with one embodiment of the present invention. Catheter 12 has a closed distal end 18 and an exit port 24 located along its shaft, proximal to distal end 18. Catheter 12 further includes at least two occlusion elements: first occlusion element 28, which is positioned between exit port 24 and ports 61 of coaxial lumen 60, and distal occlusion element 55, which is positioned between exit port 24 and distal end 18 of catheter 12. Coaxial lumen 60 and ports 61 can be supply lumen 20 with inlet ports 26, or auxiliary delivery lumen 23 and secondary exit ports 25. First occlusion element 28 is designed to separate an area for receiving thermally altered blood (i.e. the target site) from an area supplying normothermic blood to control unit 14, or from an area receiving supplemental blood at a different temperature $T_2$. Distal occlusion element 55 is designed to act as an anchor, while also separating an area for receiving thermally altered blood (the target site) from an untreated area. In a preferred embodiment, first and distal occlusion elements 28 and 55 include radiopaque markers 48 for allowing for positioning of catheter 12 within the blood vessel.

Figure 7A:
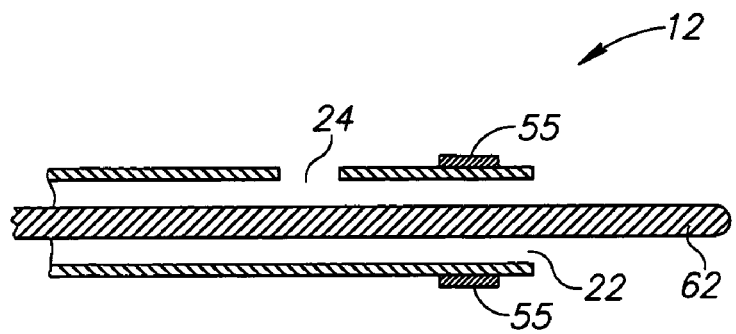
FIGS. 7A-7C are illustrations of a distal portion of a catheter which is suitable for anchoring in a separate vessel, in accordance with another embodiment of the present invention.
Figure 7B:
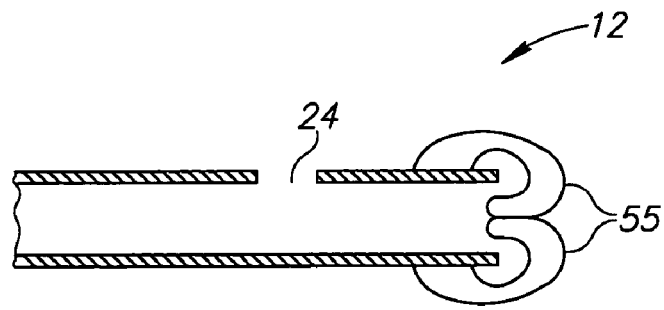
Figure 7C:
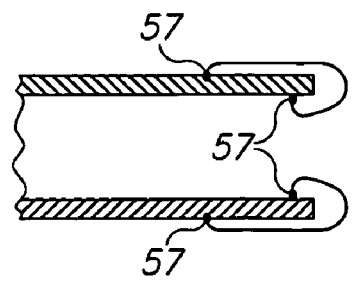

Reference is now made to FIGS. 7A and 7B, which are illustrations of a distal portion of catheter 12, suitable for anchoring in a separate vessel, in accordance with another embodiment of the present invention. As shown in FIG. 7A, guidewire 62 is introducible through delivery lumen 22. In an alternative embodiment, catheter 12 includes a separate guidewire lumen (not shown) either coaxial with or alongside delivery lumen 22. Catheter 12 includes a distal occlusion element 55, which in one embodiment is an inflatable balloon designed to extend over distal end 18 upon inflation. As shown in FIG. 7B, inflation of distal occlusion element 55 results in expansion of the balloon over distal end 18, causing the delivery lumen to be sealed. This type of configuration can be accomplished, for example, by attaching the balloon to the catheter shaft near the distal end of the catheter, such that upon inflation, the balloon is configured to expand over the edge of catheter 12. Alternatively, distal occlusion element 55 can have multiple attachment points 57, as shown in FIG. 7C in a deflated state, which dictate a direction of expansion for distal occlusion element 55. Exit port 24 is located on the shaft of catheter 12, and is positioned proximal to distal occlusion element 55.

It should be readily apparent that in all of the described embodiments, additional lumens may be included for various purposes. For example, a lumen for oxygenation of blood may be added. Additional cooling/heating lumens or additional lumens to control flow or pressure may be added as well.

In a preferred embodiment, system 10 is used to provide hypothermia for treatment of stroke. A target temperature for cooling is in the range of 18 to 30 degrees Celsius, and may be maintained for hours or days. The system described herein also allows for gradual rewarming of the treated area by slowly introducing blood of different temperatures.

Reference is now made to FIGS. 8A-C, which are illustrations of a method for treating a specific target site in accordance with a preferred embodiment of the present invention. As shown in FIG. 8A, catheter 12 is inserted into a blood vessel, and advanced to a vessel which is adjacent to the target site, referred to hereinafter as adjacent vessel 100. In a preferred embodiment, catheter 12 is initially inserted into a blood vessel such as the brachial, femoral or radial artery. In a preferred embodiment, wherein the goal is to selectively cool the brain without induction of systemic hypothermia, the target site is the brain, and adjacent vessel 100 is the internal carotid artery. A position of catheter 12 within adjacent vessel 100 is monitored by visualization of radiopaque marker 48. When catheter 12 is in the desired location, occlusion element 28 is expanded, as shown in FIG. 8B. This expansion primarily serves to isolate a particular section of adjacent vessel 100 which leads to the target site, thereby preventing normothermal blood from flowing into the target organ, and can also help anchor catheter 12 in place. Reference is now made to FIG. 8C, which illustrates the flow of blood. Once occlusion element 28 is deployed, normothermic blood, represented by arrows 44, enters supply lumen 20 via inlet ports 26. This blood flows through supply lumen 20, out through inlet connector 32 of hub 30 and through supply blood inlet 34 into control unit 14. Control unit 14 then heats or cools the blood to form thermally altered blood, which is pumped out through delivery blood outlet 38, through outlet connector 36, and into delivery lumen 22. Thermally altered blood, represented by broken arrow 46, flows out through exit port 24 and into the portion of the blood vessel which leads to the target site. In one embodiment, pharmaceuticals are simultaneously administered to the target site via drug infusion port 52. In another embodiment, sensors located at or near the exit ports measure physiological parameters such as pressure, flow and temperature, and the data is sent to control unit 14. Control unit 14 compares the received data to desired settings and adjusts heating/cooling as required. This cycle can continue for as long as is necessary for the particular application. In a preferred embodiment, the cycle is repeated for 1-72 hours.

Reference is now made to FIGS. 9A-C, which are illustrations of a method for treating a specific target site in accordance with another embodiment of the present invention. As shown in FIG. 9A, catheter 12 is inserted into a blood vessel, and advanced to a vessel which is adjacent to the target site, referred to hereinafter as adjacent vessel 100. In a preferred embodiment, catheter 12 is initially inserted into a blood vessel such as the brachial, femoral or radial artery. In a preferred embodiment, wherein the goal is to selectively cool the brain without induction of systemic hypothermia, the target site is the brain, and adjacent vessel 100 is the internal carotid artery. A position of catheter 12 within vessel 100 is monitored by visualization of radiopaque marker 48. When catheter 12 is in the desired location, occlusion element 28 and second occlusion element 54 are both expanded, as shown in FIG. 9B. Occlusion element 28 and second occlusion element 54 can be sequentially or simultaneously expanded. Expansion of occlusion element 28 primarily serves to isolate a particular section of blood vessel 100 which leads to the target site, and can also help anchor catheter 12 in place. Expansion of second occlusion element 54 serves to separate an area for delivery of supplemental blood, which is of a different temperature $T_2$ than a temperature $T_1$ of thermally treated blood sent to the target site, and from normothermic blood returning through supply lumen 20. Reference is now made to FIG. 9C, which illustrates the flow of blood. Once occlusion element 28 and second occlusion element 54 are deployed, normothermic blood, represented by arrows 44, enters supply lumen 20 via inlet ports 26. This blood flows through supply lumen 20, out through inlet connector 32 of hub 30 and through supply blood inlet 34 into control unit 14.

Control unit 14 then heats or cools the blood to form thermally altered blood, which is pumped out through delivery blood outlet 38, through outlet connector 36 and into delivery lumen 22. Thermally altered blood, represented by broken arrow 46, flows out through exit port 24 and into the portion of the blood vessel which leads to the target site. In addition, supplemental blood, represented by wide arrows 47, is sent through auxiliary delivery lumen 23 and into a secondary vessel 101, which may lead to a secondary target site. In one embodiment, pharmaceuticals are simultaneously administered to the target site and/or to the supplemental blood via drug infusion port 52. In another embodiment, sensors located at or near the exit ports measure physiological parameters such as pressure, flow and temperature, and the data is sent to control unit 14. Control unit 14 compares the received data to desired settings and adjusts heating/cooling as required. This cycle can continue for as long as is necessary for the particular application.

Figure 10C:
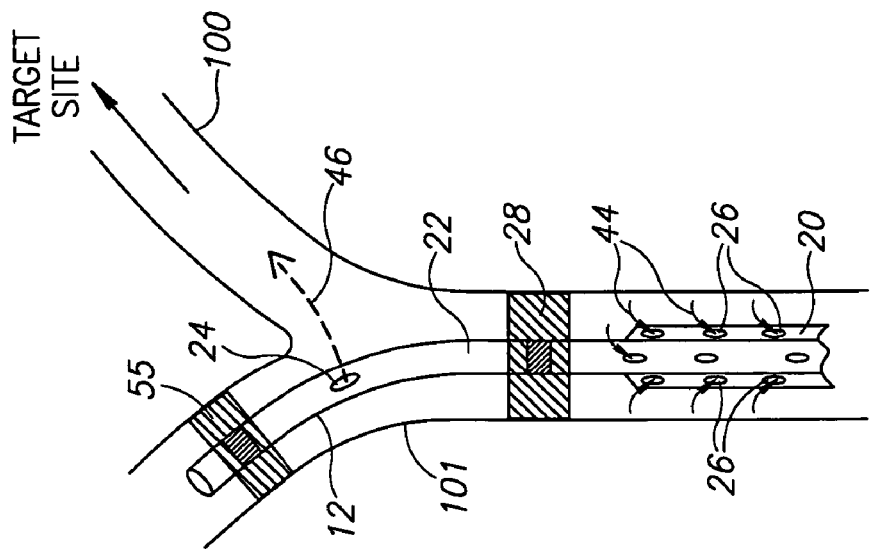
FIGS. 10A-10C are illustrations of a method for treating a specific target site in accordance with yet another embodiment of the present invention.
Figure 10B:
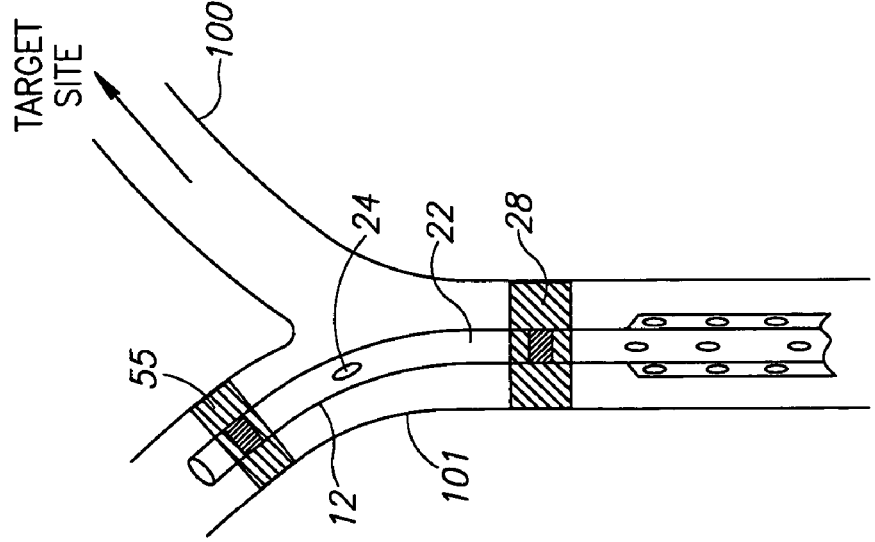
Figure 10A:
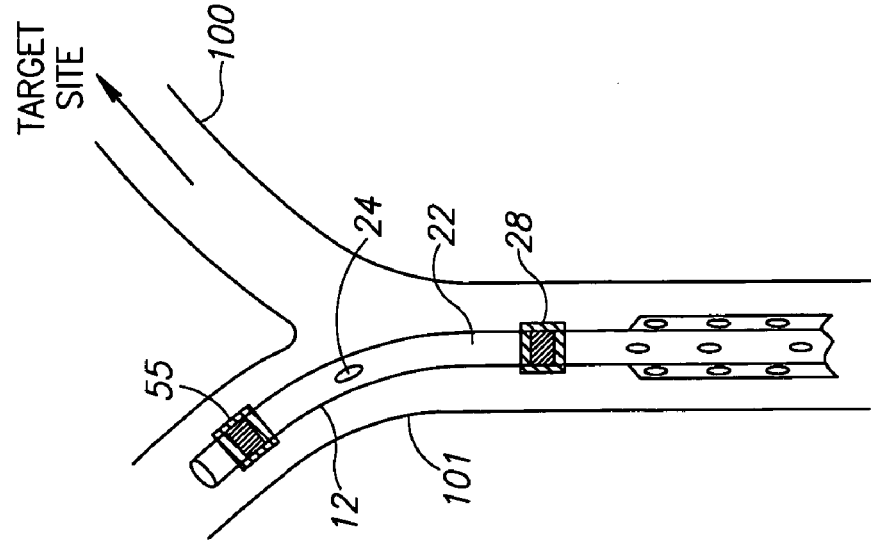

Reference is now made to FIGS. 10A-C, which are illustrations of a method for treating a specific target site in accordance with yet another embodiment of the present invention. As shown in FIG. 10A, catheter 12 is inserted into a blood vessel, and advanced to a secondary vessel 101 which is near adjacent vessel 100. For example, adjacent vessel 100 and secondary vessel 101 can be branches of a vessel. This method may be desirable, for example, if adjacent vessel is diseased and might be adversely affected by introduction of a foreign element such as a catheter therein. In a preferred embodiment, catheter 12 is initially inserted into a blood vessel such as the brachial, femoral or radial artery. In a preferred embodiment, wherein the goal is to selectively cool the brain without induction of systemic hypothermia, the target site is the brain, and secondary vessel 101 is the external carotid artery. A position of catheter 12 within vessel 101 is monitored by radiopaque marker 48. When catheter 12 is in the desired location, occlusion element 28 and distal occlusion element 55 are expanded, as shown in FIG. 10B. Expansion of occlusion elements 28 and 55 serves to isolate blood vessel 100 which leads to the target site, and anchors catheter 12 in place without placing catheter 12 directly in blood vessel 100. Reference is now made to FIG. 10C, which illustrates the flow of blood. Once occlusion elements 28 and 55 are deployed, normothermic blood, represented by arrows 44, enters supply lumen 20 via inlet ports 26. This blood flows through supply lumen 20, out through inlet connector 32 of hub 30 and through supply blood inlet 34 into control unit 14. Control unit 14 then heats or cools the blood to form thermally altered blood, which is pumped out through delivery blood outlet 38, through outlet connector 36, and into delivery lumen 22. Thermally altered blood, represented by broken arrow 46, flows out through exit port 24 and into the portion of the blood vessel which leads to the target site. In one embodiment, pharmaceuticals are simultaneously administered to the target site via drug infusion port. In another embodiment, sensors located at or near the exit ports measure physiological parameters such as pressure, flow and temperature, and the data is sent to control unit 14. Control unit 14 compares the received data to desired settings and adjusts heating/cooling as required. This cycle can continue for as long as is necessary for the particular application.

It should be readily apparent that a single catheter serves to both collect and deliver the normothermic and thermally altered blood. In an additional embodiment, all or some blood contact surfaces can be coated with an anti thrombotic substance such as heparin.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for providing selective thermal therapy, the system comprising:

a first elongated element with a first wall defining a first lumen having a first lumen distal end and a first lumen proximal end and a length from said proximal end to said distal end, wherein said first lumen is a delivery lumen for delivering thermally treated blood to a target site in the body;

an exit port located on said first lumen, said exit port for delivering said thermally treated blood to the target site;

an occlusion element positioned on said first lumen, proximal to said exit port;

a second elongated element with a second wall, wherein a second lumen is defined as a space between said first wall and said second wall, and said second lumen is coaxial to said first lumen, said second lumen having a second lumen proximal end and a second lumen distal end, wherein said second lumen is a supply lumen for receiving normothermic blood from the body, said second lumen distal end positioned relative to said first lumen distal end such that said second lumen distal end is in such proximity to said first lumen distal end so that said second lumen acts as an insulating layer along a majority of said length of said first lumen when receiving the normothermic blood;

wherein said second elongated element is insertable into an artery of the body at a peripheral location of the body and adapted to extend to a remote location of the body;

an inlet positioned on said second elongated element, said inlet proximal to said occlusion element, said inlet for receiving the normothermic blood; and a control unit in fluid communication with said proximal ends of said first lumen and said second lumen, said control unit comprising:

a supply blood inlet in fluid communication with said second lumen, said supply blood inlet for receiving the normothermic blood from the body;

a thermal adjustor in fluid communication with said supply blood inlet, said thermal adjustor configured for changing a temperature of the received normothermic blood so as to provide said thermally treated blood; and a delivery blood outlet in fluid communication with said thermal adjustor and in fluid communication with said first lumen, said delivery blood outlet for providing the thermally treated blood to said first lumen.

2. The system of claim 1, wherein said exit port is located at said distal end of said first elongated element.

3. The system of claim 1, wherein said occlusion element is a balloon.

4. The system of claim 1 wherein said occlusion element has an atraumatic surface.

5. The system of claim 1, wherein said occlusion element includes a hydrophilic coating.

6. The system of claim 1, wherein said occlusion element includes a drug coating.

7. The system of claim 1, wherein said inlet comprises several inlet ports.

8. The system of claim 1, further comprising an auxiliary delivery lumen between said first and second lumens and coaxially arranged with respect to said first lumen, said auxiliary delivery lumen having a secondary exit port positioned between said exit port and said inlet.

9. The system of claim 8, wherein said secondary exit port comprises several secondary exit ports.

10. The system of claim 8, further comprising a second occlusion element positioned between said secondary exit port and said inlet.

11. The system of claim 1, further comprising an auxiliary delivery lumen and said second port is a secondary exit port, the supply lumen positioned coaxially with respect to said auxiliary delivery lumen.

12. The system of claim 11, wherein said secondary exit port comprises several secondary exit ports.

13. The system of claim 11, wherein said inlet port comprises several inlet ports.

14. The system of claim 11, further comprising a second occlusion element positioned between said secondary exit port and said inlet.

15. The system of claim 1, further comprising an anchoring element at said distal end of said first lumen.

16. The system of claim 15, wherein said anchoring element is the occlusion element.

17. The system of claim 15, wherein said anchoring element is a bent distal end.

18. The system of claim 1, wherein said control unit includes a pumping mechanism.

19. The system of claim 1, further comprising a physiological sensor positioned at said exit port.

20. The system of claim 19, wherein said physiological sensor is in communication with said control unit, said control unit configured to calculate an output based on data received from said physiological sensor.

21. The system of claim 20, wherein said output is presented as a display to a user.

22. The system of claim 20, wherein said output is used to automatically change a parameter provided by said control unit.

23. The system of claim 1, wherein said inlet is located at said second lumen distal end.

24. The system of claim 1, wherein the peripheral location is a femoral artery, a brachial artery, or a radial artery.

25. The system of claim 1, wherein the remote location is a brain.

26. The system of claim 1, wherein the inlet is one or more ports.

27. The system of claim 1, wherein said first elongated element and said second elongated element are insertable into an artery of the body at a peripheral location of the body, wherein, in use, said second elongated element extends from the peripheral location distally into the body to reach a remote location in the body whereby a majority of said second elongated element is located beyond the peripheral location until it extends further than only shortly distally into the artery, and
wherein said second elongated element extends a distance beyond only shortly distally into the body such that without the insulating layer the body would be adversely cooled.

28. The system of claim 1, wherein said second lumen is juxtaposed with said first lumen.

29. A device for providing selective thermal therapy, the device comprising:
   a first elongated element with a first wall, a delivery lumen defined by a space within the first wall;
   a second elongated element with a second wall, a supply lumen defined by a space between the first wall and the second wall;
   a control unit in fluid communication with said supply lumen and said delivery lumen, the control unit comprising:
   a supply blood inlet in fluid communication with said supply lumen, said supply blood inlet for receiving normothermic blood from the body; and
   a delivery blood outlet in fluid communication in fluid communication with said delivery lumen, said delivery blood outlet for providing thermally the thermally treated blood to said delivery lumen,
   wherein the supply lumen delivers normothermal blood to the control unit located outside of the body;
   wherein the delivery lumen receives thermally treated blood from the control unit and supplies the thermally treated blood to a target site in the body, wherein the supply lumen is coaxial to said delivery lumen wherein said supply lumen is positioned around a majority of said delivery lumen so that said supply lumen acts as the insulating layer along a majority of said delivery lumen when receiving the thermally treated blood, and wherein said supply lumen, the control unit and said delivery lumen form a closed system;
   wherein said second elongated element is insertable into an artery of the body at a peripheral location of the body and adapted to extend to a remote location of the body; and
   an occlusion element positioned on said delivery lumen in a location which is proximal to a distal end of said delivery lumen and distal to a distal end of said supply lumen.

30. The device of claim 29, wherein the control unit further includes a pumping mechanism for pumping the thermally treated blood into said delivery lumen.

31. The device of claim 29, wherein said supply lumen comprises at least one inlet port for receiving the normothermal blood, said inlet port positioned proximal to said occlusion element.

32. The device of claim 29, wherein said delivery lumen comprises at least one exit port for delivering the thermally treated blood to the target site, said exit port positioned distal to said occlusion element.

33. The device of claim 32, further comprising a second occlusion element distal to said exit port.

34. The device of claim 29, wherein said occlusion element is a balloon.

35. The device of claim 29 wherein said occlusion element has an atraumatic surface.

36. The device of claim 29, wherein said occlusion element includes a hydrophilic coating.

37. The device of claim 29, wherein said occlusion element includes a drug coating.

38. The device of claim 29, further comprising an auxiliary delivery lumen between said supply and delivery lumens and coaxially arranged with respect to said delivery lumen.

39. The device of claim 38, wherein said auxiliary delivery lumen comprises a secondary exit port.

40. The device of claim 39, wherein said secondary exit port comprises several secondary exit ports.

41. The device of claim 29, further comprising an anchoring element at said distal end of said first lumen.

42. The device of claim 41, wherein said anchoring element is the occlusion element.

43. The device of claim 41, wherein said anchoring element is a bent distal end.

44. The device of claim 29, further comprising a physiological sensor positioned at a distal end of said device.

45. The device of claim 44 wherein said physiological sensor is in communication with the control unit, the control unit configured to calculate an output based on data received from said physiological sensor.

46. The device of claim 45, wherein said output is presented as a display to a user.

47. The device of claim 45, wherein said output is used to automatically change a parameter provided by said control unit.

48. The device of claim 29, wherein the peripheral location is a femoral artery, a brachial artery, or a radial artery.

49. The device of claim 29, wherein the remote location is a brain.

50. The device of claim 29, wherein said first elongated element and said second elongated element are insertable into an artery of the body at the peripheral location of the body,
wherein, in use, said second elongated element extends from the peripheral location distally into the body to reach a remote location in the body whereby a majority of said second elongated element is located beyond the peripheral location until it extends further than only shortly distally into the artery, and
wherein said second elongated element extends a distance beyond only shortly distally into the body such that without the insulating layer the body would be adversely cooled.

51. The device of claim 29, wherein the delivery lumen is juxtaposed with said supply lumen.

* * * * *